United States Patent [19]

Dayal

[11] Patent Number: 5,789,662
[45] Date of Patent: Aug. 4, 1998

[54] METHOD AND APPARATUS FOR DETERMINING SPATIAL DISTRIBUTION OF FLUIDS MIGRATING THROUGH POROUS MEDIA UNDER VACUUM-INDUCED PRESSURE DIFFERENTIAL

[76] Inventor: Prabhu Dayal, 6601 N. Foothills Dr., Tucson, Ariz. 85718

[21] Appl. No.: 665,944

[22] Filed: Jun. 19, 1996

[51] Int. Cl.$^6$ ............................................. G01N 15/08
[52] U.S. Cl. ............................................................ 73/38
[58] Field of Search ............................................. 73/38

[56] References Cited

U.S. PATENT DOCUMENTS

| | | | |
|---|---|---|---|
| 4,649,483 | 3/1987 | Dixon | 364/422 |
| 4,868,751 | 9/1989 | Dogru et al. | 364/422 |
| 5,036,193 | 7/1991 | Davis et al. | 73/38 X |
| 5,086,643 | 2/1992 | Marek | 73/38 |
| 5,311,766 | 5/1994 | Persoff et al. | 73/38 |

OTHER PUBLICATIONS

P.J. Van Geel et al., "Laboratory and model simulations of a LNAPL spill in a variably-saturated and, 1. Laboratory experiment and image analysis techniques", *Journal of Contaminant Hydrology*, 17 (1994), pp. 1–25.

Clifford K. Ho, "An experimental investigation of air venting of volatile liquid hydrocarbon mixtures from homogenous and heterogeneous porous media", *Journal of Contaminant Hydrology*, 11 (1992), pp. 291–316.

B.H. Kueper et al., "Experimental Observations of Multiphase Flow in Heterogenous Porous Media", *Journal of Contaminant Hydrology*, 5 (1989), pp. 83–95.

J.C. Parker et al., "Experimental and Numerical Investigations of Constitutive Relations governing Multiphase Flow", Virginia Polytechnic Institute and State University, pp. 300–305.

J.C. Parker et al., "Modeling Multiphase Organic Chemical Transport in Soils and Ground Water", EPA Project Summary, EPA/600/S2-91/042, Sep. 1991; pp. 1–5.

J.C. Parker et al., "Modeling Multiphase Organic Chemical Transport in Soils and Ground Water", EPA/6500/2-91/042, Aug. 1991, pp. 171–201.

M. Oostrom et al., "Calibration and Automation of a Dual-energy Gamma System for Applications in Soil Science", Agronomy and Soils Departmental Series No. 145, Alabama Agricultural Experiment Station, Auburn University, Jun. 1990, pp. 1–16.

(List continued on next page.)

*Primary Examiner*—Hezron E. Williams
*Assistant Examiner*—Jay L. Politzer
*Attorney, Agent, or Firm*—Benman & Collins

[57] ABSTRACT

A method and apparatus are provided which determine the spatial distribution of fluids in a porous media contained in a three-dimensional cell as such fluids migrate through porous media in response to a vacuum-induced pressure differential. Specifically, the method comprises: (a) providing a three-dimensional cell including a front side and a back side, each of which are at least semi-transparent; (b) installing at least two slotted casing wells at opposing ends of the cell, at least one first slotted casing well capable of being de-pressurized and at least one second slotted casing well capable of allowing air entry into the cell; (c) filling the cell with a porous media; (d) introducing at least one fluid into the filled cell and allowing the fluid to infiltrate the porous media; (e) sealing the infiltrated, filled cell; (f) de-pressurizing the first slotted casing, thereby creating a negative pressure gradient across the infiltrated, filled cell; and (g) measuring the saturation of the fluid in the porous media at each location of interest across the plane of the front side of the three-dimensional cell. A method of use is also provided for employing the present apparatus in a pilot-scale experiment for the feasibility of recovering non-aqueous phase liquids (NAPLs) by a vacuum-based technique, such as soil vapor extraction (SVE) and vacuum-enhanced recovery (VER), depending upon the volatility of NAPL of interest.

17 Claims, 8 Drawing Sheets

OTHER PUBLICATIONS

H.O. Schiegg, "Laboratory Setup and Results of Experiments on Two–Dimensional Multiphase Flow in Porous Media", Prepared for U.S. Department of Energy, Oct. 1990, Sections 1.1–4.2.2.

"Multiphase Flow and Transport Models for Organic Chemicals: a Review and Assessment", Prepared by the University of Michigan (principal investigator: L.M. Abriola), Electric Power Institute, EA–5976, Research Project 2377–5, Sep. 1988, pp. 1–6.

R.J. Lenhard, "Measurement and Simulation of One–Dimensional Transient Three–Phase Flow for Monotonic Liquid Drainage", *Water Resources Research*, vol. 24, No. 6, pp. 853–863 (Jun. 1988).

5,789,662

METHOD AND APPARATUS FOR DETERMINING SPATIAL DISTRIBUTION OF FLUIDS MIGRATING THROUGH POROUS MEDIA UNDER VACUUM-INDUCED PRESSURE DIFFERENTIAL

TECHNICAL FIELD

The present invention relates generally to the measurement of fluid saturations in porous media, and more particularly, to the determination of fluid saturations of fluids migrating through porous media in a laboratory cell in response to a vacuum-induced pressure differential as well as the use of such determination to assess the feasibility of vacuum-induced recovery of undesirable fluids.

BACKGROUND ART

Non-aqueous phase liquids (NAPLs) such as hydrocarbon fuels, organic solvents, and other immiscible organic liquids are widely employed by industry. Through spills, leakage from underground storage tanks, and improper disposal practices, NAPLs may enter the vadose zone and possibly ultimately contaminate groundwater resources. In the event of a confirmed release of NAPLs, Underground Storage Tank (UST) regulations mandate investigation of the release, including an initial site characterization and development of a corrective action plan for free-product removal of NAPLs (e.g., diesel oil floating in wells or over the water table) before soil and groundwater remediation for the clean up of contaminants in the saturated or vadose one. Typically, free product is initially recovered by skimming or bailing of product or by pumping. Thereafter, residual NAPLs may be removed by technologies such as soil vapor extraction (SVE) and vacuum enhanced recovery (VER). The selection of the appropriate remediation technology for a given situation is governed by the type of NAPLs to be recovered and cost constraints, among other factors.

SVE has generally been the remedial option used for the recovery of highly volatile hydrocarbon species from spills of non aqueous phase liquids, such as gasoline. SVE involves the recovery of volatile phase organic hydrocarbons vaporized by vacuum induced through slotted casing wells installed in the contaminated zone. Typically, a basic SVE system pairs vapor extraction recovery wells with vacuum pumps or blowers to remove vapors, while more complex recovery systems further include trenches, air injection wells, and passive wells. SVE is most effective for the remediation of hydrocarbons of high volatility, where air is induced at a low flow rate for the evaporation of volatile organic compounds (VOCs), and also to provide oxygen for in situ biodegradation. SVE technologies are not readily applicable remediation options for non-volatile hydrocarbons such as diesel oil, which has little if any volatile organic species, depending on the age of the spill.

For the remediation of non-volatile NAPLs not amenable to removal by SVE, one may employ vacuum enhanced recovery (VER). VER is an in-situ remediation process that induces flow and recovery of NAPLs by vacuum extraction through slotted casing recovery wells. However, depending on the cost and feasibility of VER, remediation engineers and consultants may nonetheless be forced to opt for the excavation and offsite disposal of contaminated soils or leave the contaminants in place with no remedial action.

Numerous numerical codes have been developed to evaluate and design various remediation strategies for the removal or extraction of NAPLs from contaminated sites with heterogeneous soil and complex hydrogeology. Three-phase models have been found to be very useful to estimate and predict NAPL flow and design remediation plans and assess the associated costs and risks involved in the process. A few of these three-phase models applicable for air-water-NAPL flow in three dimensions claim to be useful in the design of SVE and VER remediation systems. However, very few of these models are tested against experimental three-phase flow data and it is believed that none of these models are tested specifically against experimental three-phase vacuum-induced flow data.

It is noted that although it would be preferred to test models against data from NAPL-contaminated field sites rather than against laboratory results, controlled field experiments for NAPL remediation would be very expensive and time-consuming. Using data from existing NAPL-contaminated sites would also be difficult due to the inability to accurately establish initial and boundary conditions such as duration, quantity, rate and time of NAPL leak or spill.

There are known experimental techniques available for studying multiphase flow in 2-D cells used in qualitative visual or photo imaging techniques to track the movement of red-dyed NAPLs. For example, Ho et al conducted such an experiment for volatile liquid hydrocarbon mixtures. C. K. Ho et al, "An Experimental Investigation of Air Venting of Volatile Liquid Hydrocarbon Mixtures from Homogeneous and Heterogeneous Porous Media", *Journal of Contaminant Hydrology*, 11, 1992, pp. 291–316. The experiment was designed to investigate the vapor phase of volatile organics in soil using visual observations of the red dyed plume movement through heterogeneous media. Experimental results delineated the vaporization modes of single and binary hydrocarbon liquids held in homogeneous and heterogeneous porous media during air venting. A vacuum pump was used to induce airflow through the sand pack, and a flowmeter at the entrance was used to measure the flow rate. Gas samples were taken from a sampling bulb at the exit of the apparatus.

However, none of the qualitative visual or photo imaging techniques directly measure the fluid saturations of NAPL and water in porous media. Therefore, these experimental techniques cannot be accurately used to predict the feasibility of VER or SVE in a particular application nor to validate mathematical models of VER or SVE.

In contrast, there are experimental techniques that directly measure fluid saturations. An example of such experimental flow data used to validate a mathematical model is found in Parker et al, "Modeling Multiphase Organic Chemical Transport In Soils And Ground Water", U.S. EPA Report No. EPA/600/2-91/042, Ada, Okla., August 1991. Parker et al. conducted 2-D multiphase laboratory experiments using a dual-energy gamma attenuation system and hydrophobic and hydrophilic tensiometers for measuring two-phase pressures and saturations to develop multiphase flow and transport models. Specifically, Parker et al conducted laboratory studies in a 1×1.5×0.85 meter sand tank to validate the infiltration and redistribution of both light and dense NAPLs in a single coarse soil texture. Essentially, Parker et al performed the five stages of (1) water drainage; (2) NAPL infiltration; (3) NAPL redistribution; (4) water flushing; and (5) NAPL entrapment.

The use of a dual-energy gamma attenuation system by Parker et al accurately assessed fluid saturations of NAPLs and water in porous media—this technology has been long established and is based upon the theory of Beer's law. Specifically, the attenuation of gamma radiation (I) through a soil with dry bulk density ($\rho$) and volumetric water content ($\theta_w$) can be written using the subscripts s, w and g to denote soil, water and gas phase, respectively:

$$I=I_0\exp(-\mu_s\rho_s x-\mu_w\rho_w\theta_w x-\mu_g\rho_g\theta_g x) \quad (1)$$

where $I_0$ is the empty cell count rate in counts per second (cps)

I is the emergent count rate (cps)
$\mu_i$ is the mass attenuation coefficient of phase i
x is the path length of the gamma beam through i
$\rho_i$ is the density of phase i
$\theta_g$ is the volumetric gas phase content
$\theta_w$ is the volumetric water content.

When simulating a vacuum-enhanced recovery process, one substitutes $U_w$ for ($\mu_w\rho_w$) and ignores the contribution of the gas phase to the attenuation of the photons, such that equation (1) becomes $$I=I_0\exp(-\mu_s\rho_s x-U_w\theta_w x) \quad (2)$$

It is noted that the contribution of the gas phase would not be ignored in a simulation of SVE.

Substituting subscripts (c) and (a) for the $^{137}$Cs and $^{241}$Am gamma radiation to form two equations and then solving these equations yields the bulk density ($\rho_s$):

$$\rho_s = \frac{U_{wc}\ln(I_{oa}/I_a) - U_{wa}\ln(I_{oc}/I_c)}{x(\mu_{sa}U_{wc} - \mu_{sc}U_{wa})} \quad (3)$$

While Parker et al employed $^{137}$Cs and $^{241}$Am in their dual-energy gamma attenuation system, any two gamma sources with gamma energies that are different such that their mass attenuation coefficients are sufficiently different may theoretically be employed. Specifically, $^{137}$Cs emits gamma radiation at about 662 KeV after β decay, while $^{241}$Am gamma rays have an energy of about 60 KeV after α decay. Other applications have employed $^{137}$Cs and $^{170}$Tm for dual-energy gamma sources instead of $^{241}$Am and $^{137}$Cs for measuring fluid saturations.

However, none of the experimental determinations of fluid saturations in porous media using dual-energy gamma attenuation systems, including Parker et al, conduct experimental flow data in which the infiltrated NAPLs and water are subject to a vacuum-induced pressure differential. It follows that there is presently no experimental method in use to accurately evaluate the effectiveness of such vacuum-based remediation techniques such as SVE and VER.

A need remains for a method and apparatus to model the three-phase flow of NAPL, water, and air through porous media under the influence of a vacuum-induced pressure gradient, including the ability to directly measure the fluid saturations of the phases. Additionally, a need remains for a method for assessing the feasibility of VER and SVE remediation techniques as well as for calibrating mathematical models describing such techniques.

DISCLOSURE OF THE INVENTION

In accordance with the present invention, a method and apparatus are provided which determine the spatial distribution of fluids in a porous media contained in a three-dimensional cell as such fluids migrate through porous media in response to a vacuum-induced pressure differential. Specifically, the method comprises the steps of employing the below-described three-dimensional cell:

(a) providing a three-dimensional cell including a front side and a back side, each of which are at least semi-transparent;

(b) installing at least two slotted casing wells at opposing ends of the cell, at least one first slotted casing well capable of being de-pressurized and at least one second slotted casing well capable of allowing air entry into the cell;

(c) filling the cell with a porous media;

(d) introducing at least one fluid into the filled cell and allowing the fluid to infiltrate the porous media;

(e) sealing the infiltrated, filled cell;

(f) de-pressurizing the first slotted casing, thereby creating a negative pressure gradient across the infiltrated, filled cell;

(g) collimating a beam of gamma or X-ray of radiation on the front side of the infiltrated, filled cell at each location of interest across the plane of the front side of said three-dimensional cell; and (h) measuring the amount of radiation exiting the back side of the cell at each location of interest and therefrom determining the saturation of the at least one fluid in the porous media at each location of interest across the plane of the front side of the three-dimensional cell.

A method of use is also provided for employing the present apparatus in a pilot-scale experiment for the feasibility of recovering NAPL by a vacuum-based technique, namely SVE and VER, depending upon the volatility of the NAPL of interest.

Therefore, the present method and apparatus provide an accurate means to determine in pilot-scale the three-phase saturations of an oil spill as it redistributes from the surface through the heterogeneous soils in the vadose zone to the water table, followed by vacuum enhanced recovery or soil vapor extraction of free product or volatile phase in a slotted casing extraction well and recovery system. Accordingly, remediation consultants and regulators are afforded the capability to assess and test vacuum enhanced recovery system designs and validate models under controlled laboratory simulations that represents site conditions before they are installed at soil and ground water remediation sites at extensive cost. The two step procedure also enables controlled laboratory scale verification and testing of three-phase models or codes by simulating sequential experimental stages for the vacuum-based recovery of NAPL and volatile hydrocarbons.

Three-phase modeling codes that have been successfully tested with experimental data allow investigators to have confidence that the code will predict the field behavior reasonably well, provided that the site is accurately characterized and the model parameters are adequately calibrated to the site.

BEST MODES FOR CARRYING OUT THE INVENTION

A method and apparatus are provided which determine the spatial distribution of fluids in a porous media contained in a three-dimensional cell as such fluids migrate through porous media in response to a vacuum-induced pressure differential. Specifically, the method comprises the following steps, each of which will be discussed in greater detail below:

(a) providing a three-dimensional cell including a front side and a back side, each of which are at least semi-transparent;

(b) installing at least two slotted casing wells at opposing ends of the cell, at least one first slotted casing well capable of being de-pressurized and at least one second slotted casing well capable of allowing air entry into the cell;

(c) filling the cell with a porous media;

(d) introducing at least one fluid into the filled cell and allowing the fluid to infiltrate the porous media;

(e) sealing the infiltrated, filled cell;

(f) de-pressurizing the first slotted casing, thereby creating a negative pressure gradient across the infiltrated, filled cell; and (g) measuring the saturation of the fluid in the porous media at each location of interest across the plane of the front side of the three-dimensional cell.

Figure 1:
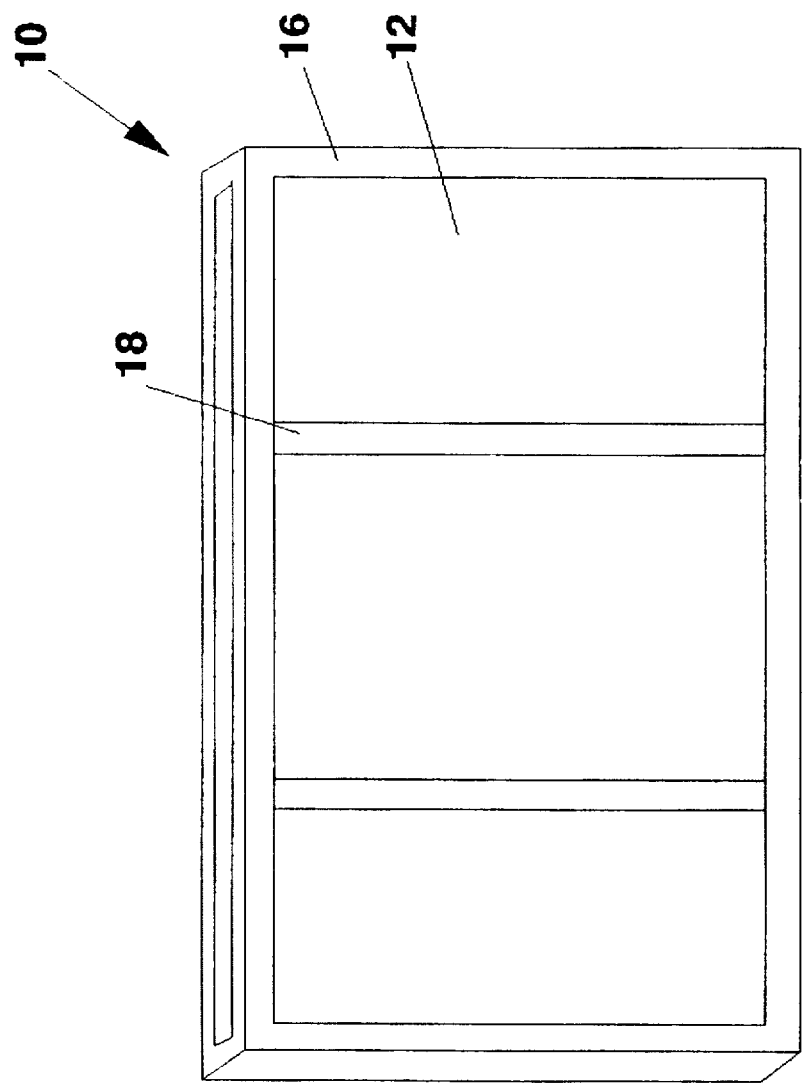
FIG. 1 is a simple perspective view of the cell portion of the apparatus employed in the practice of the invention.

FIG. 1 depicts a three-dimensional representation of the cell 10 employed in the method of the invention and as part of the present apparatus. The cell 10, although three-dimensional, approximates a two-dimensional cell, given its narrow width. In a preferred embodiment of the invention, the cell 10 is 1 meter high, 1.5 meters long, and 0.08 meters wide, such that its front side 12 and back side (identical to front side on opposite side of cell, not shown) have an areal extent of 1.5 m². Although the front side 12 and back side of the cell 10 of the preferred embodiment are rectangular in shape, it is contemplated that the sides of the cell may assume any shape, so long as the resulting cell 10 is capable of containing the porous media; the cell thickness is such that fluid saturations within the porous media may be measured; and the cell 10 may be sealed to achieve a negative pressure gradient. For example, it is contemplated that the front and back sides might have curved or even circular outlines.

It is contemplated that the front side 12 and back side of the cell 10 be substantially transparent such that the fluid saturations within the porous media may be visible in addition to being measurable, such as by a gamma radiation system. Specifically, the preferred method of measuring fluid saturations in the practice of the invention involves using a dual-energy gamma ray attenuation system, which may require that the cell 10 be at least semi-transparent along the path of measurement. Thus, it is preferred that the front side 12 and back side of the three-dimensional cell 10 be made of a material that is at least semitransparent and strong enough to contain the porous media without buckling. Moreover, the front side 12 and back side should be resistant to attack by the fluids introduced into the porous media, such as certain organic chemicals. An example of a suitable material is plastic, such as an amber semitransparent plastic such as Ultem® Plexiglass®, commercially available from Rohm & Haas. To further buttress the front and back sides of the cell 10, it is contemplated that a metal frame 16 and cross braces 18 are installed about the cell 10.

The cell 10 is equipped with at least two slotted casing wells at opposing ends. These wells are illustrated in the schematic of the laboratory apparatus presented as FIG. 2, which represents a plan view of the front side 12 of the cell 10. At least one well 20 is devoted to providing a negative pressure gradient to induce flow of the fluids contained within the porous media, thereby simulating fluid flow under the influence of a vacuum. Additionally, at least one well 22 is devoted to providing air entry. The slotted casings for the wells 20 and 22 preferably contain some means of preventing the well from plugging due to inflow of porous media. For example, the use of a gravel pack and wire mesh within the slotted casing is specifically contemplated in the practice of the invention to prevent such porous media as sand and clay from plugging the wells 20 and 22.

The vacuum induced in the slotted casing wells 20 may be accomplished by any available means. It is specifically contemplated that, to achieve a negative pressure gradient in the practice of the invention, a vacuum pump 24 is connected to the slotted casing wells 20 and is operated after sealing the cell 10. Any degree of negative pressure gradient that may be safely withstood by the cell 10 may be employed in the practice of the invention. It is further contemplated that the negative pressure induced by the vacuum pump 24 will be controlled by a vacuum control 26 and that the pressure itself will be monitored, such as by a simple U-tube manometer 28.

Figure 2:
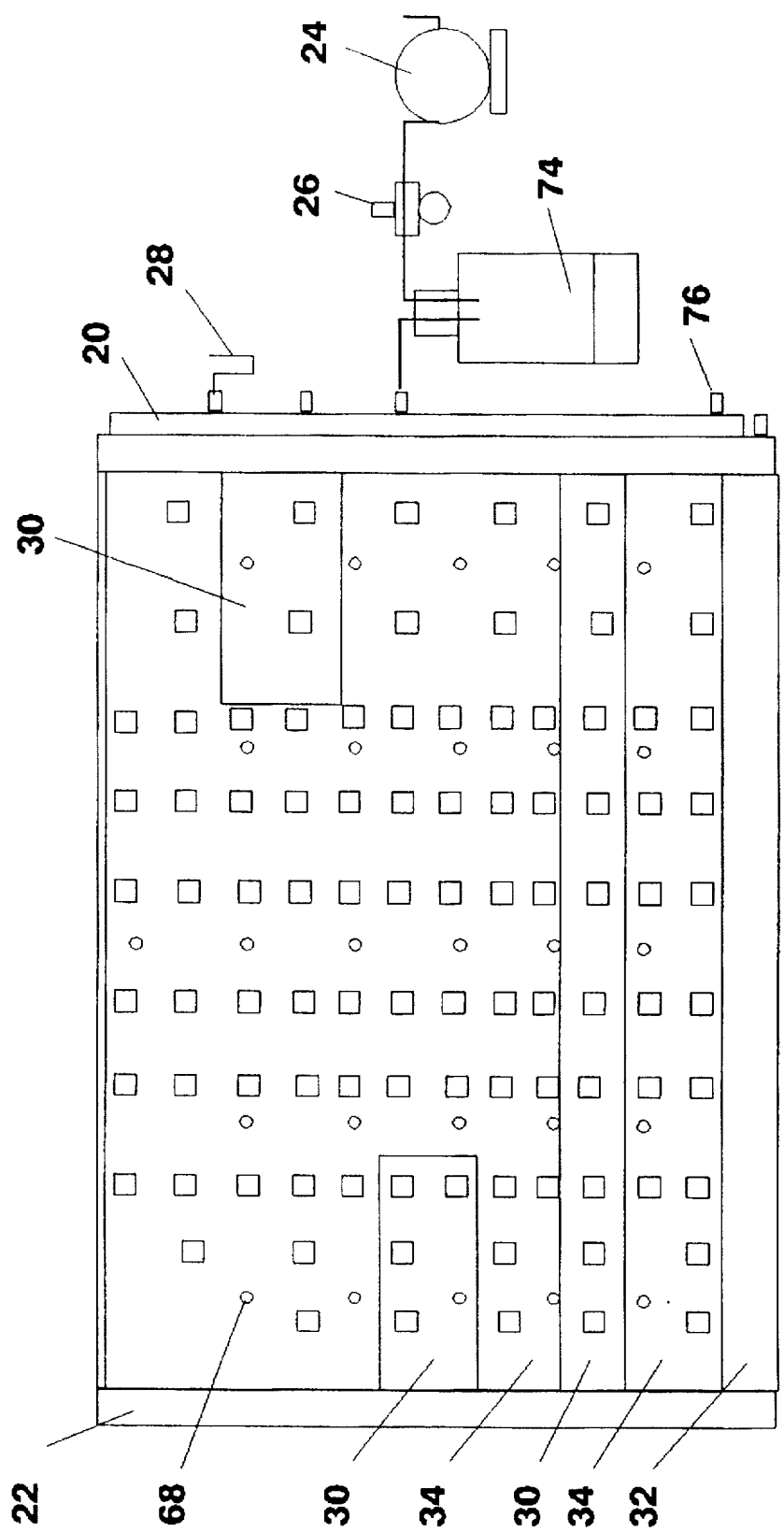
FIG. 2 is a schematic of the laboratory apparatus employed in the practice of the invention and the types of porous media contained therein for purposes of the examples.

The porous media placed into the cell 10 may be any porous media through which the fluid of interest might flow in response to a negative pressure gradient. Specifically, it is contemplated that the porous media comprise a naturally-occurring earth material such that the porous media in the cell 10 simulates soil conditions of interest for fluid migration. Examples of naturally-occurring earth materials include clay, sand, and silt. It is also contemplated that the porous media will comprise a heterogeneous mixture of materials of known but different textures to establish boundary conditions within the cell 10. For example, layers of clay, sand, and silt might be employed to simulate soil conditions in a particular area of NAPL contamination. In the Example below, Areas 30 represented Type 1 clay while Areas 32 and 34 represented Types 1 and 2 sands, respectively, having characteristics as reported in Table 1 below. Thus, the schematic of FIG. 2 illustrates an essentially vertical layering of porous media within the cell 10.

In addition to the air introduced into the cell 10 by means of the slotted well 22, it is contemplated that at least one additional fluid is introduced into the cell for infiltration into the porous media. While the fluid may be either gaseous or liquid in phase, it is preferred that at least one liquid be introduced into the cell 10. However, any fluid of interest may be introduced thereinto for response to the vacuum-induced negative pressure gradient. Examples of possible fluids of interest include NAPLs, although the invention is not so limited. It is specifically contemplated that the porous media mimic earth materials in situ, such that water is also introduced into the cell 10. Therefore, it is preferred that, in addition to the introduction of air, water and the NAPL of interest are introduced into the cell 10 to infiltrate the porous media.

Typically, the introduction of a water and the NAPL of interest into the cell 10 involves four stages, each of which may be studied. First, the water is allowed to redistribute within the porous media, reflecting changes in water table and capillary fringe. Then, the NAPL is allowed to infiltrate and re-distribute within the porous media. Finally, the water and NAPL migrate through the porous media in response to a negative pressure gradient induced by vacuum at one of the slotted casing wells 20. In this manner, one essentially models the migration of a NAPL through a porous media that might be expected following a spill of the NAPL onto soil and the eventual remediation of the soil by vacuum, such as VER or SVE or combinations thereof.

Figure 3:
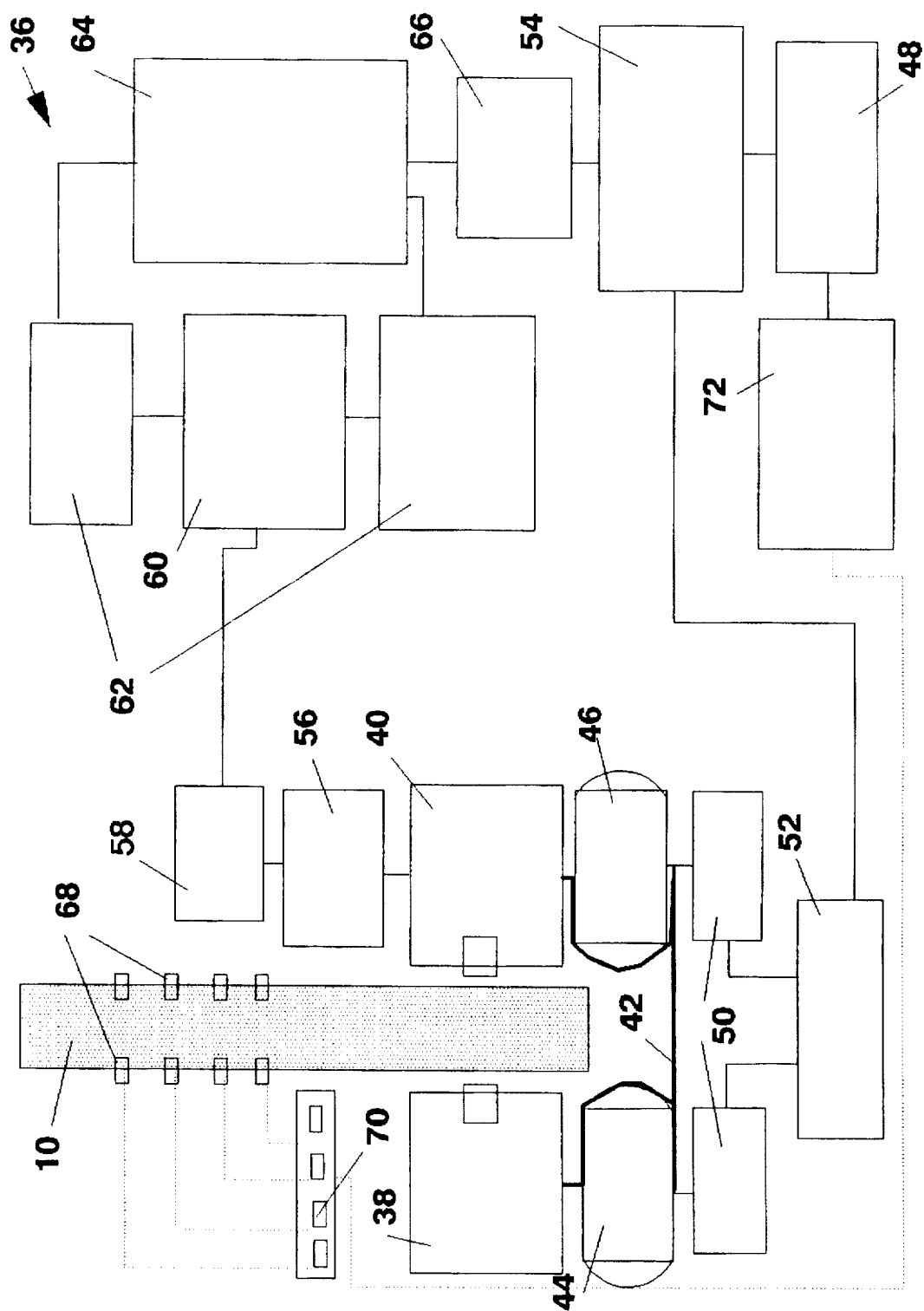
FIG. 3 is a schematic of the instrumentation employed in the dual-energy gamma radiation system for the preferred embodiment of the invention to measure fluid saturations in the cell.

The manner of simultaneously and continuously measuring the fluid saturations of interest throughout the porous media is specifically contemplated to be a dual-energy gamma attenuation system, although the invention is not so limited. For example, an X-ray fluorescence system might also be employed, among other options. FIG. 3 represents a flow diagram of a typical dual-energy gamma radiation system 36. The mechanical part of the dual-energy gamma ray attenuation system 36 consists of the source 38/detector 40 assembly which is mounted on a movable platform 42 on parallel steel rails about the cell 10, shown in a side view. A stable voltage source 41 provides necessary power to the detector 40. The interconnected sources 38 and detector 40 can be moved simultaneously, either horizontally or vertically, by horizontal 44 and vertical 46 stepper motors connected to an arrangement of chain and gear drives (not shown). The platform 42 supports and maintains axial alignment of the radiation source 38 and detector 40. The horizontal 44 and vertical 46 stepping motors are used to drive and position the system using a microprocessor-based controller 48. The stepper motor control units 50 can be activated manually or by computer control. The actuator 52 serves as an intermediate controlling device, interfacing between the stepper motor control units 50 and the data acquisition board 54 in the computer. In the preferred embodiment, the system 36 is capable of moving and taking repeat measurements at any position within its 2 meter horizontal or 1.1 meter vertical range to within 0.5 mm. A heavy steel table (not shown) is welded between the tracks to provide a stable support for clamping the soil cell 10.

In the preferred embodiment, the gamma radiation source 38 consists of two distinct energy ranges of 60 and 662 KeV mounted coaxially in a custom lead alloy shield (not shown). The sources 38 are standard sealed capsules; one preferably contains 200 mCi $^{137}$Cs and the other 100 mCi $^{241}$Am. The Cs source is located in the center, while the Am source is placed at the front end of the shield. Typically a thallium-activated crystal of sodium iodide (not shown) is used to detect the transmitted radiation from the gamma detector 40. The scintillations produced from the incident gamma rays are contemplated to be converted into electrical pulses in a 10-stage photomultiplier tube (not shown) which is built into the detector crystal package 40. The detector package 40 is mounted in a custom manufactured, lead alloy shield with collimation provided by cylindrical holes, preferably about 6.35 mm in diameter. Pulses leaving the photomultiplier tube are shaped and amplified in a preamplifier 56. These pulses are again amplified in a gain-stabilized amplifier 58. Once amplified, the electrical pulses are linearly transmitted through an automatic gain control unit 60, to a pair of single channel pulse height analyzers 62 (SCA). The SCAs 62 convert the shaped linear pulses into countable pulses by using its integral or differential discriminator (not shown). Radiation intensities are determined by first filtering out the pulses that represent energies outside of the window of interest. Counting and timing functions are performed in a 4-channel precision counter/timer module 64. Three of the channels are used for counting operations and the fourth is used in timing. This module 64 also contains the remote communications circuitry (not shown) to allow remote control of the counter/timer functions. The timer/multiscaler 64 is connected to the data acquisition board 54 via a buffered interface card 66. The computer 48 is used to instruct the timer/multiscaler 64 to start and stop counting via the buffered interface 66 where data is stored temporarily in its buffer.

It is noted that a plurality of ports 68 for tensiometers may be incorporated into the cell 10 in order to measure pressure at various locations of interest within the cell 10. A plurality of pressure measurement ports 68 is likewise depicted in FIG. 2 as being distributed across the plane of the cell 10 (see small circles). Tensiometers may be 15 installed in the ports 68 as incorporated into the back and front 12 sides of the cell 10, then being connected to transducers 70. The analog data from these transducers 70 is converted to digital data in an A to D converter 72 and is then sent to the microprocessor 48. These ports 68 for tensiometers may also be used to measure pressures in the cell locations by injecting an instrument called a Tensimeter® (available from Soil 20 Measurement Systems of Tucson, Ariz.). Specifically, the needle of the Tensimeter® is inserted through a septum at the location of the tensiometer.

The derivations of equations and procedures used for the determination of attenuation coefficients, path lengths, bulk densities and fluid saturations from the dual-energy gamma system data are detailed below, as demonstrated by Parker et al., in "Modeling Multiphase Organic Chemical Transport In Soils and Ground Water", U.S. EPA Report No. EPA/600/2-91/042, Ada, Okla., August 1991.

First, the attenuation coefficients must be determined. Assuming $^{241}$Am and $^{137}$CS sources, the attenuation coefficients for NAPL, soils and water, for example, may be determined by the following known procedure using a small Plexiglass cell with 4 compartments of known widths which represent the path lengths (x) (see, e.g. R. J. Lenhard et al., "Measurement and Simulation of One-Dimensional Transient Three-Phase Flow for Monotonic Liquid Drainage", *Water Resources Research*, Vol. 24, No. 6, pp. 853–63 (June 1988)). The method employs a compartmentalized calibration cell of known path lengths for taking exiting radiation measurements through the cell with varying number of chambers filled with the material of interest. Linear regression programs may be used to evaluate the product of the attenuation coefficient and density of the material $(-\mu_i \rho_i)$ according to the linearized form of Beers Law for a radioactive beam (I) passing through a fluid I:

$$\ln(I) = \ln(I_o) - \mu_i \rho_i x \tag{4}$$

This method provides several points at different path lengths to determine $-\mu_i \rho_i$ from the Cesium and Americium counts.

Determinations of path lengths and bulk densities must be calculated for each location of interest across the front side 12 of the cell 10 at which fluid saturation measurements are desired. Due to variation of cell thickness after filling with soil and water, accurate path lengths (x) for each of the measurement locations are calculated from the $^{241}$Am and $^{137}$Cs counts for the empty cell and the water filled cell:

$$x = (1/\mu_i \rho_i) \cdot \ln(I_o/I) \tag{4a}$$

where $\mu_i$ and $\rho_i$ are the known gamma radiation attenuation coefficient and mass density, respectively.

Bulk densities and water contents at each measurement location in the cell can now be calculated from Equation 5 using the measured Americium and Cesium gamma radiation counts passing through a porous medium containing water and air as fluids, the corresponding path lengths (x), gamma radiation attenuation coefficients ($\mu_i$) and empty experimental cell counts ($I_o$). The attenuation of gamma radiation (I) through a soil with dry bulk density (ρ) and volumetric water content ($\theta_w$) can be written using the subscripts s, w and g to denote soil, water and gas phase, respectively:

$$I = I_0 \exp(-\mu_s \rho_s x - \mu_w \rho_w \theta_w x - \mu_g \rho_g \theta_g x) \quad (5)$$

where $I_0$ is the empty cell count rate in counts per second (cps)

I is the emergent count rate (cps)

$\mu_i$ is the mass attenuation coefficient of phase i x is the path length of the gamma beam through i $\rho_i$ is the density of phase i $\theta_g$ is the volumetric gas phase content.

Substituting $U_w$ for ($\mu_w \rho_w$) and ignoring the contribution of the gas phase to the attenuation of the photons, equation (5) becomes $$I = I_0 \exp(-\mu_s \rho_s x - U_w \theta_w x) \quad (6)$$

Substituting subscripts (c) and (a) for the $^{137}$Cs and $^{241}$Am gamma radiation to form two equations and then solving these equations yields the bulk density ($\mu_s$):

$$\rho_s = \frac{U_{wc} \ln(I_{od}/I_a) - U_{wa} \ln(I_{od}/I_c)}{x(\mu_{sc} U_{wc} - \mu_{sc} U_{wa})} \quad (7)$$

The fluid saturations within the cell 10 may be determined from the $^{137}$Cs and $^{241}$Am counts using Beers Law relationship. The gamma ray attenuation (I) through a porous medium with water (w), NAPL (n) and gas (g) can be written as:

$$I = I'_0 \exp(-\mu_s \rho_s x - \mu_w \rho_w \theta_w x - \mu_g \rho_g \theta_g x) \quad (8)$$

where $I'_0$ is the count rate through the empty column in cps $\mu_n$ is the NAPL attenuation coefficient $\rho_n$ is the density of NAPL $\theta_n$ is the volumetric NAPL content.

Assuming the contribution of the gas phase to be negligible (unless simulating an SVE process) and assuming the bulk density is constant with time, equation (8) can be rewritten as $$I = I_0 \exp(-\mu_w \rho_w \theta_w x - \mu_n \rho_n \theta_n x) \quad (9)$$

where $I_0 = I'_0 \exp(-\mu_s \rho_s x)$.

Substituting subscripts (c) and (a) for $^{137}$Cs and $^{241}$Am gamma radiation to form two equations and then solving these equations yields the water ($\theta_w$) and NAPL ($\theta_n$) contents:

$$\theta_w = [\mu_{na} \rho_n x \ln(I_{od}/I_c) - \mu_{nc} \rho_n x \ln(I_{od}/I_a)]/y \quad (10)$$

$$\theta_n = [\mu_{wc} \rho_n x \ln(I_{od}/I_c) - \mu_{wa} \rho_n x \ln(I_{od}/I_a)]/y \quad (11)$$

where $y = (\mu_{wc} \rho_w x)(\mu_{na} \rho_n x) - (\mu_{wa} \rho_w x)(\mu_{nc} \rho_n x)$.

Thus, in a preferred embodiment, one may pack the cell 10 with porous media, introduce air, water, and the NAPL of interest into the cell 10, and measure the fluid saturations of the water and NAPL at desired locations across the back and front 12 sides of the cell 10 by substituting data measured by a dual-energy gamma radiation system 36 in equations (10) and (11) above.

The fluid saturation data acquired in the practice of the invention is contemplated for use in several applications. For example, the porous media in the cell 10 may be selected and placed to simulate an actual contaminated zone and the fluids introduced into the cell 10 may be selected to match those actually spilled into such a zone, such that the feasibility of vacuum-based remediation techniques such as VER and SVE may be assessed on a pilot scale before committing to such clean-up operations on a large scale in an actual spill site. Specifically, one would be able to analyze the migration of fluids through the pilot-scale model as well as calculate an anticipated recovery of NAPL for a VER- or SVE-based clean-up operation. In a related application, one might study the fluid migration of oil and gas through porous media in response to vacuum-induced negative pressure gradients, which represents in pilot-scale the recovery of oil and gas via slotted casing wells. In addition to the simple primary recovery of oil and gas in porous media, one might also add various chemicals or fluids, such as carbon dioxide or steam, to study the secondary and tertiary recovery of oil and gas in porous media in a pilot-scale apparatus.

Another contemplated application of the present pilot-scale apparatus is the assessment and optimization of computer models used to predict the behavior of fluids undergoing VER, SVE, or "bioslurping", which is a combination of SVE and VER. Essentially, the experimental results from the present pilot-scale apparatus, as operated under controlled boundary conditions, may be compared to the predictive results from a model, such that the model may be calibrated to match the experimental results. In this fashion, the accuracy of the model in regard to application to vacuum-based recovery of fluids in heterogeneous soils should be improved. Testing the effectiveness of three-phase models to simulate VER of non-volatile NAPL free-product such as diesel oil or SVE of volatile NAPLs in controlled 2-D laboratory scale investigations prior to installation at VER or SVE remediation sites could be used in lieu of expensive field testing to meet regulatory requirements or clean-up standards.

The usefulness of the disclosed method and apparatus are contemplated to extend to many fields and applications, of which assessment of the feasibility of VER and SVE are two of many. Others include bioslurping, venting, bioventing, and air sparging. The method and apparatus of the invention are demonstrated below in the following example.

EXAMPLE

The method of the invention was used to study, in pilot-scale, the spatial distributions of three-phase fluid saturations after an oil spill simulation from the surface at the 100-cm elevation of the cell 10 as migration occurred through the vadose zone during the sequential stages of infiltration, redistribution and vacuum enhanced recovery (VER). Particularly, the laboratory experiments were performed in a three-dimensional cell 10 having the dimensions of 1 m high×1.5 m long×0.08 m wide, such as illustrated in FIG. 1. The front side 12 and back side of the cell 10 were made of amber semitransparent plastic (Ultem) which is resistant to organic chemicals. The frame 16 was made of steel with cross braces 18 installed on both sides to prevent bulging of the cell 10. A strong frame 16 was necessary because the accuracy of measurements from the gamma system are affected by any variation to the path lengths (thickness of cell). Accurate path lengths were determined by using equations from the gamma system's Am and Cs data. An automated dual-energy gamma attenuation system 36 such as described above as the preferred embodiment was used for the simultaneous continuous measurement of NAPL and water saturations.

In particular, the stepper motor control units 50 employed were Model SP 155A from Superior Electric of Bristol, Conn.; the actuator 52 was Model Aston 800 from Aston Company of Georgia; the gamma detector 40 was from Harshaw Chemical of Solon, Ohio; the data acquisition board 54 was Model MBC IEEE 4888 from Keithley MetraByte Corporation of Taunton, Mass.; the buffered interface card 66 was Model TC 489 from Tennelec of Oak Ridge, Tenn.; and the Tensimeters® were manufactured by Soil Measurement Systems of Tucson, Ariz. Specifically, Tensimeters® are injection-type devices used to measure pressure. In contrast, tensiometers (which may be alternatively employed) are employed for hydrophilic and hydrophobic pressure measurement, having been coated and treated in a laboratory.

FIG. 2 depicts the types of porous media employed in this example as well as the general layout of the heterogeneous soil packing placement in the cell 10. Horizontal clay layers were dispersed within layers of sand, with Areas 30 representing Type 1 Clay while Areas 32 and 34 represent Types 1 and 2 sands, respectively. Specifically, Type 1 sand was packed at the bottom of the cell 10 to an elevation of about 13 cms to simulate the saturated zone and a 10-cm thick Type 1 clay layer was packed at an elevation of 30 cms across the entire length of the cell. Two smaller Type 1 clay layers were placed on the left side of the cell 10 at an elevation of 55 cms and on the right side of the cell at an elevation of 67 cms. The remainder of the heterogeneous soil packed in the cell 10 constituted Type 2 sand. The clay barriers were used to illustrate the experimental simulation capability and accuracy of NAPL and water saturation measurements in heterogeneous porous media. Table 1 below lists the initial moisture content, dry bulk density, porosity and particle density for the types of sands and clay used:

TABLE 1

Summary Of Moisture Content, Bulk Density, Porosity And Particle Density.

| Iden-tifica-tion | Initial Moisture Content Gravimetric (%, g/g) | Volumetric (%, cm$^3$/cm$^3$) | Dry Bulk Density (g/cm$^3$)(%) | Calculated Porosity (g/cm$^3$) | Particle Density |
|---|---|---|---|---|---|
| Type 1 Sand | 33.0 | 50.2 | 1.52 | 43.0 | 2.67 |
| Type 2 Sand | 23.7 | 38.7 | 1.63 | 40.2 | 2.73 |
| Type 1 Clay | 47.4 | 55.6 | 1.17 | 57.0 | 2.73 |

The gamma system was capable of moving and taking repeat measurements at any position within its 2 meter horizontal or 1.1 meter vertical range to within 0.5 mm. A heavy steel table (not shown) was welded between the tracks to provide a stable support for clamping the soil cell 10. A series of gamma radiation counts of 5 minutes in duration were taken at 96 locations across the front side 12 of the cell 10 as programmed with a map file; each of these 96 programmed grid positions are shown in FIG. 2 as signified by squares 73. The gamma radiation counts were accomplished at of the 96 grid positions 73 by moving two interconnected parallel platforms 42, one supporting the radiation sources 38 and the other supporting the gamma detector 40, via stepper motors 44 and 46 under computer 48 control. In the automatic mode of operation, the computer 48 read positions data from a pre-defined map file and moved the source 38/detector 40 to the selected map location 73 on the cell 10, thereby making possible automatic, unattended system operation experiments for long durations and repetitious experiments at predetermined times.

Two rectangular slotted casing wells 8 cms wide×5 cms were installed at each end of the cell. One well 20 was designed to enable vacuum enhanced recovery and the other well 22 was designed for air entry. The slotted casing was designed using a fine wire mesh and a gravel pack just outside the wells 20 and 22 to prevent the sand and clays from plugging the wells. The vacuum extraction system used a graduated flask 74 for NAPL and water retrieval hooked up to a variable vacuum pump 24. The top of the cell 10 was sealed during the VER stage of the experiment.

The Americium and Cesium windows were first calibrated to correct for Compton scattering before a systematic calibration of the cell 10. The $^{137}$CS and $^{241}$Am spectra were calibrated by using the pulse height analyzer 62 to plot each spectrum and adjusting the high voltage setting and the coarse gain setting in such a way that the base line voltage was at the ideal energy ratio to the gamma radiation. Since the amplified output pulses had a broad energy spectrum it was necessary to discriminate these pulses for the identification of the energy spectra of both sources. The $^{137}$Cs spectrum was determined by using the pulse height analyzer 62 and plotting the data spectrum.

Correction for Compton-scattered $^{137}$Cs photons detected in the $^{241}$Am window was necessary since a single detector 40 was used to simultaneously determine $^{241}$Am and $^{137}$Cs photons. Compton-scattered $^{137}$Cs photons cause interference in the $^{241}$Am window. Compton scattering will cause photons to deflect from their original path while giving up some of their energy. The interference of Cs in the Am spectrum is caused by Compton scattering in the detector 40, and the amount of scattering at a given Cs intensity is independent of the absorbing material. To determine the amount of Compton scattering, which is the low energy Cs, the collimator of the source holder 38 was covered with thin brass plates and variable amounts of glass and plexiglass placed in the beam path and the count rates recorded in all 3 channels (Am, Cs and Integrated) for 300 seconds. The brass plates prevented Am radiation from reaching the detector 40. Count rates of the low energy window were plotted against those of the high energy. A regression program was used to calculate the correlation between the high energy Cs counts and the low energy Cs counts in the Americium window. The data points were fitted by using a third order polynomial, which was subsequently used to correct the $^{241}$Am count rates by subtracting the low energy Cs count from the total count observed in the low energy window.

Following the completion of calibrating the gamma sources 38, a systematic calibration of the cell 10 was performed by the determination of Am and Cs counts for (1) the empty cell, (2) water-filed cell, (3) dry soil- and clay-packed cell, and (4) water saturated cell packed with soil and clay. The Am and Cs counts from this calibration sequence were used to determine the path length (thickness of cell), bulk densities, NAPL and water saturations at each of the 96 locations of interest 73 indicated in FIG. 2 using Beer's Law relationship in the equations described above.

The heterogeneous soils and clays were initially packed dry in the cell 10 using the soil configuration shown in FIG. 2. Am and Cs counts were taken at the 96 grid locations 73 using the automated feature of the gamma system 36 to obtain the dry soil measurements required for calibration. The cell 10 was then water saturated completely by adding water through the bottom port in the cell until the water-table elevation coincided with the upper soil boundary. Am and Cs counts were again taken at the same 96 grid locations 73 using the automated feature of the gamma system 36 to obtain the water-saturated soil measurements. During each of these calibration stages, gamma counts at the 96 grid locations 73 were taken for 300 seconds using two repetitions. The cell 10 was then considered ready for the experimental simulation of water drainage to establish initial conditions followed by the NAPL spill experiment. Table 2 below reports the attenuation coefficients determined for the apparatus of the example:

TABLE 2

Summary of Attenuation Coefficients $(-\mu, \rho_1)$.

| Identification | $^{241}Am$ | $^{137}Cs$ |
| --- | --- | --- |
| Water | 0.197552 | 0.08458 |
| NAPL | 0.760684 | 0.071456 |
| Soil | 0.250384 | 0.078785 |

Once the cell 10 was calibrated and initial conditions established with a water saturated soil cell, the NAPL spill evaluation was performed in four stages. Am and Cs counts were taken continuously for 90 seconds at each at the 96 programmed cell locations 73 to determine NAPL and water saturations during the experimental stages of (1) water redistribution, (2) NAPL infiltration, (3) NAPL redistribution, and (4) VER. The collection of data at the end of each stage was used as the representative boundary conditions for the start of the next stage during modeling exercises. This required documentation of the exact time when each of the sequential stages were completed and the next stage began in a continuous manner.

Stage 1: Water Redistribution. The top of the cell 10 was covered to prevent water evaporation losses. The water in the cell 10 was then allowed to drain through the side ports 76 located 10 cms from the bottom until steady state conditions were obtained with the water table at 10 cms elevation. Am and Cs readings were taken at all 96 grid locations 73 during the water redistribution to enable plotting the water saturation contours during the redistribution process through the heterogeneous soils.

Stage 2: NAPL Infiltration. NAPL was infiltrated at the soil surface at the top center of the cell 10 over an area of 25 cm² using gravity feed through a set of 6 distribution tubes from a calibrated bottle before the start of the experiment. Soltrol-170, a branched alkane solvent manufactured by Phillips Petroleum of Bartlesville, Okla. and having a density of about 0.83 g cm$^{-3}$, was used to simulate light non-aqueous phase liquid (LNAPL) in the oil infiltration and VER phase of the experiment. To enable clear differentiation between the attenuation factors for LNAPL and water, the Soltrol-170 was spiked with the addition of 1-iodoheptane at a volumetric mixture at a ratio of 1:9. The addition of 1-iodoheptane to the Soltrol-170 increased the $^{241}Am$ attenuation coefficient to 0.95 cm² g$^{31\ 1}$, a five fold increase compared to the original Soltrol-170 $^{241}Am$ attenuation coefficient of 0.18 cm²g$^{-1}$.

More particularly, the LNAPL was introduced into the cell 10 at a steady flow rate of about 2 liters/hour, such that about 9 liters were introduced into the cell in 4.5 hours. The NAPL was fed using a graduated flask (not shown) fitted with an adjustable valve and 6 small flow tubes (not shown) to facilitate NAPL infiltration on the soil surface over an area of 5cms×5 cms. Am and Cs counts were taken using a special map file that enabled the tracking of the plume close to the spill source during infiltration.

Stage 3: NAPL Redistribution. The Am and Cs counts were continued following NAPL infiltration to track the redistribution of NAPL and water in the heterogeneous soils for 20 hours.

Stage 4: Vacuum Enhanced Recovery. After NAPL redistribution reached steady state conditions, the top of the cell 10 was sealed air tight and the vacuum pump 24 hooked up to the VER well 20. Air entry was through the vent well 22 located on the opposite end of the cell 10. Vacuum extraction was started at 34 mb of vacuum. The vacuum was slowly increased to 57 mb which raised the water level in the extraction well 20. NAPL and water were recovered in a graduated flask 74 hooked up as shown in FIG. 2. After 12 hours the extraction rate was increased to 67 mb. The final vacuum extraction rate was increased to 100 mb for a total of 28 hours. The rate of NAPL and water extracted in the graduated flask 74 was measured. The vacuum was measured using a mercury manometer 28. A Tensiometer® was used to measure the air vacuum in the soil by insertion of the measurement needle through the septum stopper located at a pressure measurement port 68.

The raw data consisting of Am and Cs counts at the 96 locations 73 at various time intervals were converted to NAPL and water saturations using the procedures described earlier. The average of two sets of data obtained for NAPL and water saturations, one each from the Am and Cs counts, was used.

FIGS. 4A through 4D represent a series of contour plots showing NAPL and water saturations aerially across the back and front 12 sides of the cell 10 as measured in centimeters. The location of the clay layers 30 were superimposed on the graphs as dotted lines. A smoothing algorithm was employed to smooth the plots. It is noted that one could also plot fluid saturations against time for each of the 96 grid locations 73.

Figure 4A:
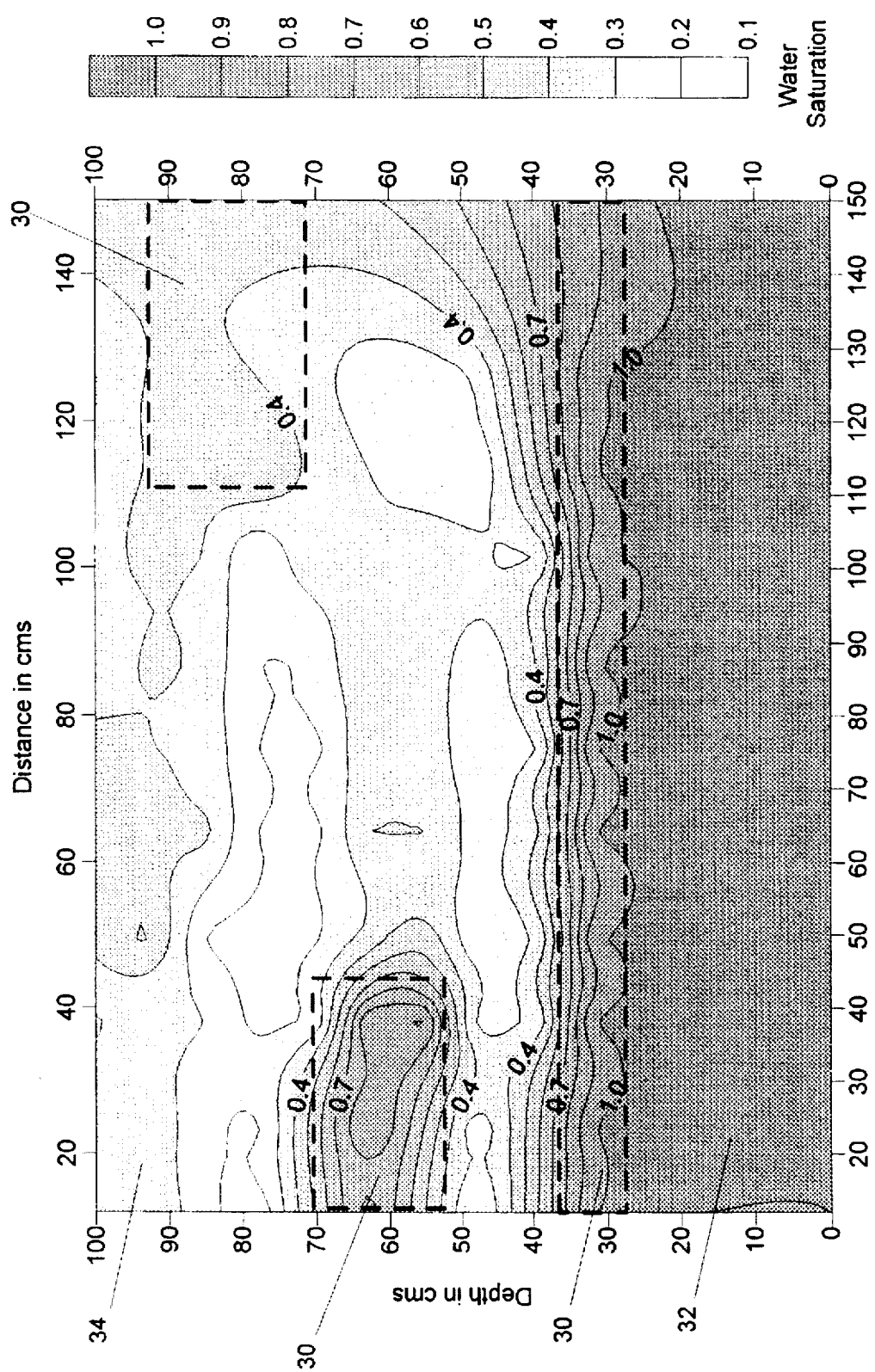
FIGS. 4A–4D are contour plots over the entire matrix of grid locations of the cell of measured NAPL and water saturations.

Stage 1: Water Redistribution. FIG. 4A represents a contour plot of measured water saturations for the experimental soil configuration after water redistribution. The water redistribution contours after 30 hours show the water table and capillary fringe at the 30-cm to 40-cm elevation with saturations from 1.0 to 0.4. The Type 1 clay layer 30 located on the left side of the soil cell at the 60-cm elevation retained moisture over 0.80 even after 30 hours. The clay layer located on the right side of the cell at the 70-cm elevation retained moisture at about 0.40, as shown by the measured water redistribution contours. This contour plot of measured water saturations shows the significantly higher moisture retention characteristics of the Type 1 clays 30 compared to the sand layers 32 and 34. These results agree with the high porosity clays at 60% compared to 40% porosity for sands used in this experiment.

Figure 4B:
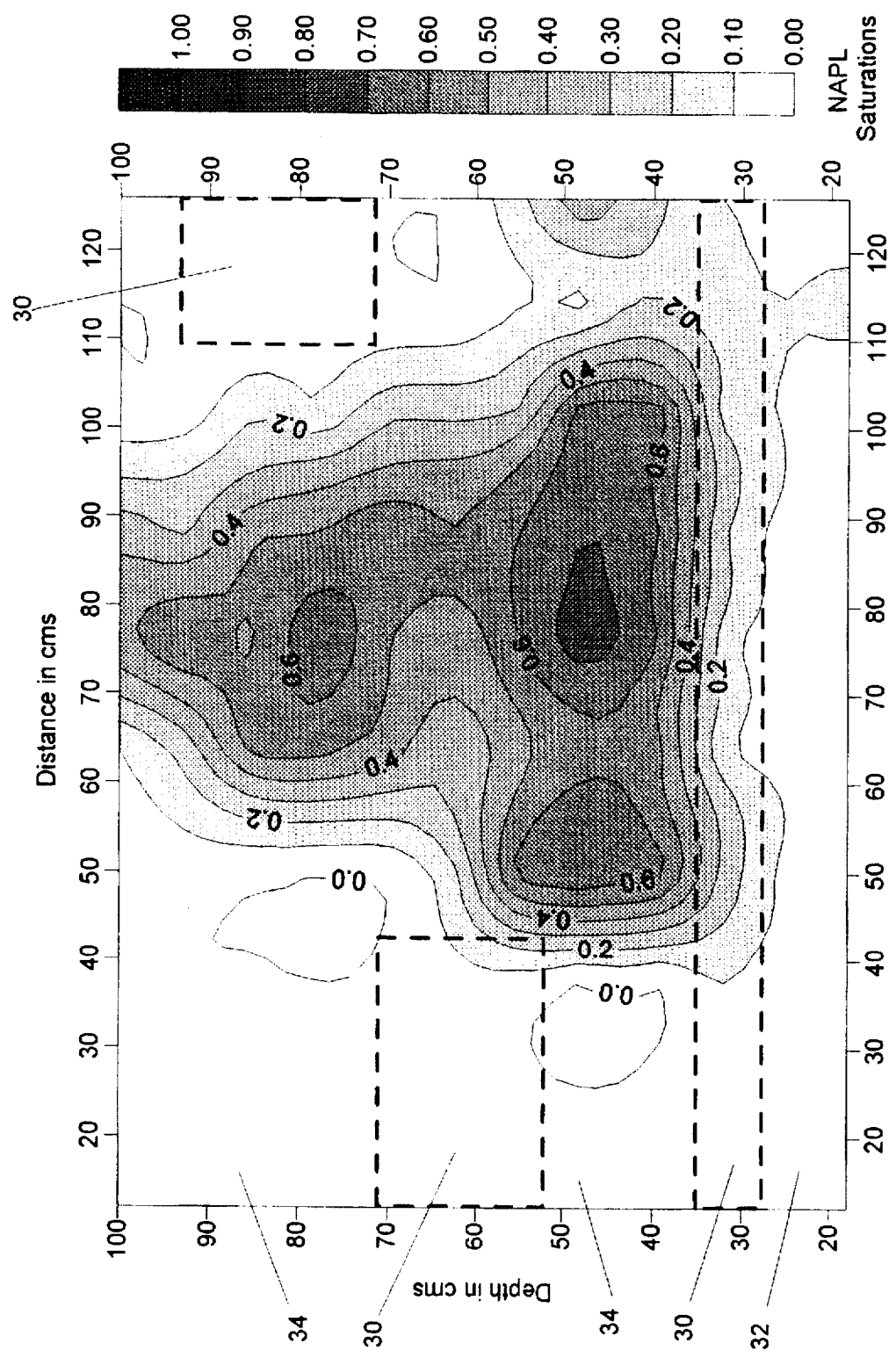

Stage 2: NAPL Infiltration. FIG. 4B represents a contour plot of measured NAPL saturations and water redistribution for the experimental soil configuration after 3 hours of NAPL infiltration. The NAPL plume for 9 liters of NAPL was found to spread above the clay layer 30 at the 40-cm elevation. The water retention in the Type 1 clay layer 30 at the 60-cm elevation on the left side of the cell seems to have prevented the NAPL from penetrating the clay to the left. NAPL saturations were found close to 0.80 in the center of the plume at the 45-cm elevation, where the clay barrier 30 prevented vertical downward migration.

Figure 4C:
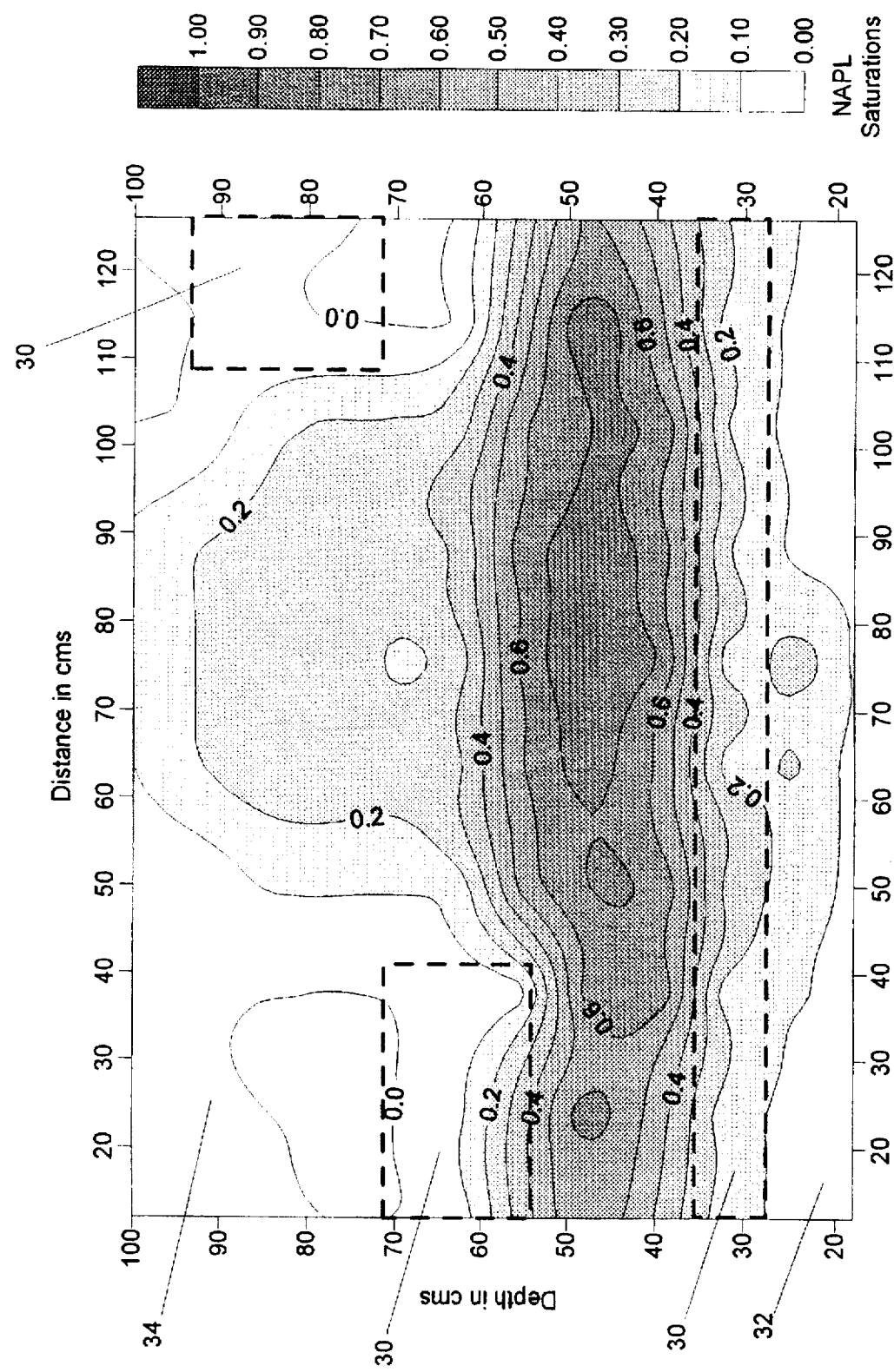

Stage 3: NAPL Redistribution. FIG. 4C represents a contour plot of measured NAPL saturations for the experimental soil configuration after NAPL redistribution after 9 hours. The clay layer 30 at the 30-cm elevation, which retained water at a saturation of 0.7 to 1.0, only allowed NAPL entry to saturations of 0.0 to 0.3. This illustrates the mass balance of volume occupied by the three phases NAPL-water-air in the soil pores. It appears that there was very little trapped air in these voids, based on the saturations of NAPL and water at these locations. No NAPL saturations were generally present below the clay layer 30 in the water table.

Figure 4D:
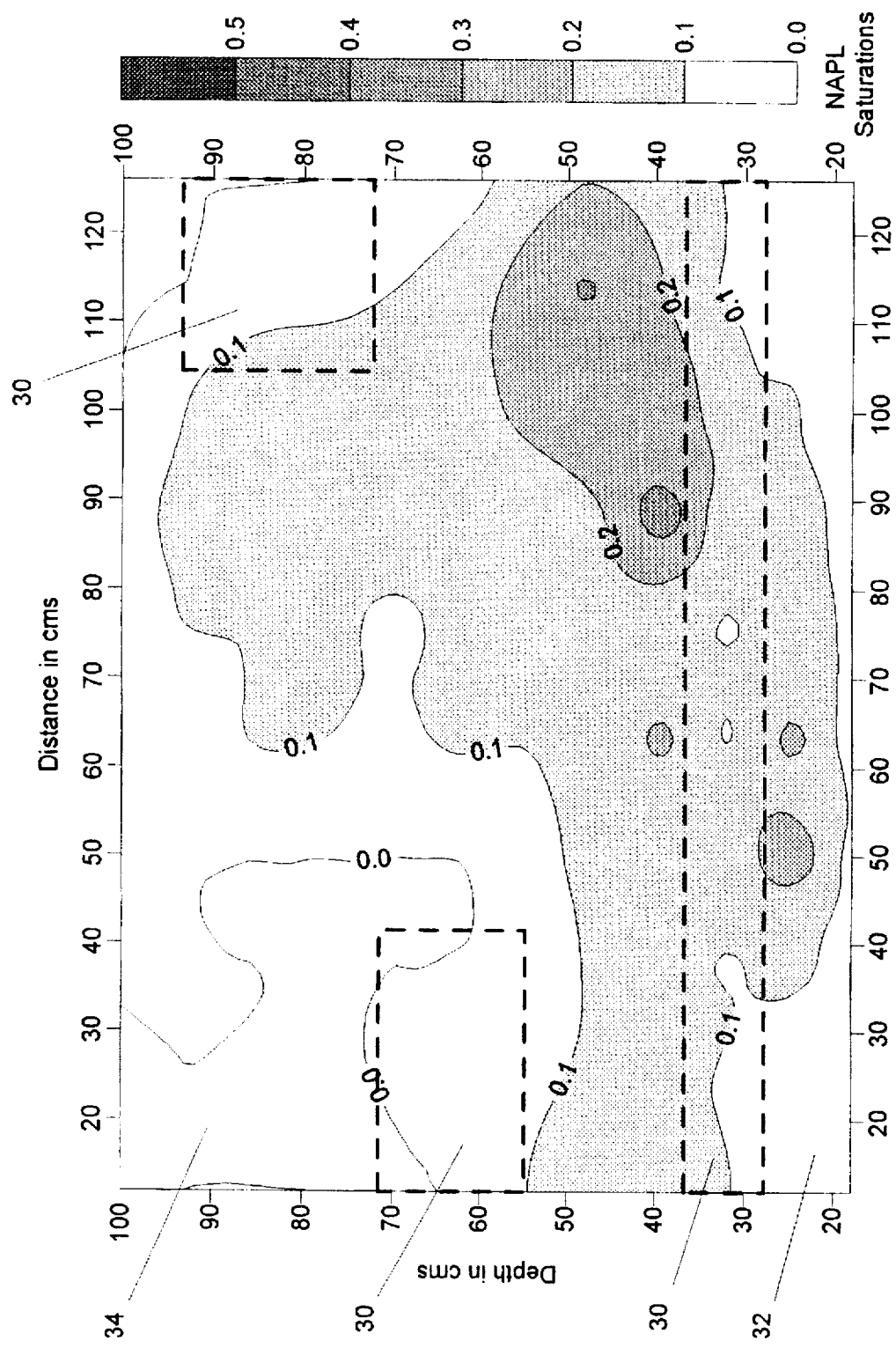

Stage 4: Vacuum Enhanced Recovery. FIG. 4D represents a contour plot of measured NAPL saturations for the experimental soil configuration after 28 hours of VER, which successfully extracted a relatively large percentage of the NAPL. The maximum retention of NAPL saturation is shown plotted at about 0.20 near the lower right side of the cell in FIG. 4D. The rest of the contour plot indicate a reduction in the NAPL saturation to below 0.10. The vacuum extraction rate at 100 mb could attribute to the recovery of NAPLs.

The accuracy of the gamma system 36 for the measurement of NAPL retention in the soil was evaluated by comparing the actual retention volume with that measured by the gamma system 36. This accuracy analysis was performed by comparing the measured NAPL retention volume calculated by integrating measured NAPL saturations at 96 locations 73 in the cell 10 with the actual NAPL retention derived from the volume recovered by the VER system in the flask 74. The actual retention volume was derived by subtracting the NAPL volume recovered in the VER extraction system from the original infiltration volume of 9,000 ml. The measured retention volume of NAPL was calculated by integrating the measured NAPL saturations at the 96 locations 73, using the porosity of the soil and the volume represented for each location, as shown:

$$\Phi_i = 1 - (\rho_{bi}/\rho_{pi}) \text{ (for } i = 1, 96) \quad (12)$$

$$V_{ni} = \theta_{ni} \times \Phi_i \times V_i \text{ (where } V_i = x_i + A_i) \quad (13)$$

$$V_n = \sum_{i=1}^{i=96} V_{ni} \text{ (for } i = 1, 96) \quad (14)$$

% retention measurement accuracy $E = [(V_a - V_n)/V_a] \times 100 \quad (15)$ where $\Phi_i$, $V_i$, and $A_i$ are the calculated soil porosity, incremental porous media volume and area, respectively, for each representative location i; $\rho_{bi}$, $x_i$, and $q_{ni}$ are the soil bulk density, path length and NAPL saturation, respectively, determined by the gamma system; $\rho_{pi}$ is the soil particle density measured in the laboratory; $V_n$ is the representative NAPL volume calculated for location i; and $V_n$ is the calculated total NAPL volume in the cell 10 shown as "measured retention volume" in Table 3 below. $V_t$ is the total volume of NAPL added (here, 9000 mls) as a spill on the surface of the soil filled cell 10 and $V_r$ is the volume of NAPL recovered by VER. $V_a$ is the NAPL retention volume determined by subtracting the NAPL recovery volume by VER from the total spill volume, i.e., ($V_a=V_t-V_r$).

The total volume is the summation of NAPL volume calculated for each of the 96 positions 73. However, an area calibration factor for that represented by locations at the lower end of the cell 10 had to be made since not all 96 locations 73 were equally spaced therein. The path lengths determined by the gamma system 36 provided an accurate measure of cells thickness at each of the 96 measurement locations 73. The NAPL saturations were measured at each of the 96 location 73 using a count time of 90 seconds. Allowing for the movement time for the gamma attenuation system 36 between each location 73, the total time lapse for a complete run to measure for all 96 locations was about 2.5 hours. Due to the continuous flow of NAPL during the infiltration and VER processes, and the measurements not being instantaneous, an error is introduced in the summation of the total NAPL from the measurement of NAPL during each run at all 96 locations 73. Table 3 below shows the measured and actual (calculated by difference) NAPL volumes over the different stages of the experiment. The difference Δ ranged between 0.04 to 5.08% with a mean of 0.97%. This comparison illustrates the accuracy of the methodology used for VER measurement and further verifies the gamma system approach for measuring fluid saturations in porous media.

TABLE 3

Summary Error Analysis of Measured NAPL Retention and VER.

| Stage | Time (hrs.) | Total NAPL volume ($V_t$, ml) | VER measured recovery volume, $V_r$ (ml) | VER measured recovery volume, $V_r$ (%) | Gamma measured retention volume ($V_n$, ml) | VER measured retention volume ($V_a$, ml) | % measured retention volume Δ |
|---|---|---|---|---|---|---|---|
| NAPL infiltration | 9 | 9000 | 0 | 0 | 9364 | 9000 | +4.04 |
| NAPL redistribution | 12 | 9000 | 0 | 0 | 8975 | 9000 | −0.27 |
| NAPL redistribution | 15 | 9000 | 0 | 0 | 8600 | 9000 | −4.44 |
| NAPL redistribution | 18 | 9000 | 0 | 0 | 8542 | 9000 | −5.08 |
| VER at 57 mb | 28 | 9000 | 1700 | 18 | 7278 | 7300 | −0.30 |
| VER at 78 mb | 38 | 9000 | 3480 | 42 | 5200 | 5220 | −0.38 |
| VER at 100 mb | 58 | 9000 | 4780 | 53 | 4218 | 4220 | −0.04 |

Figure 5:
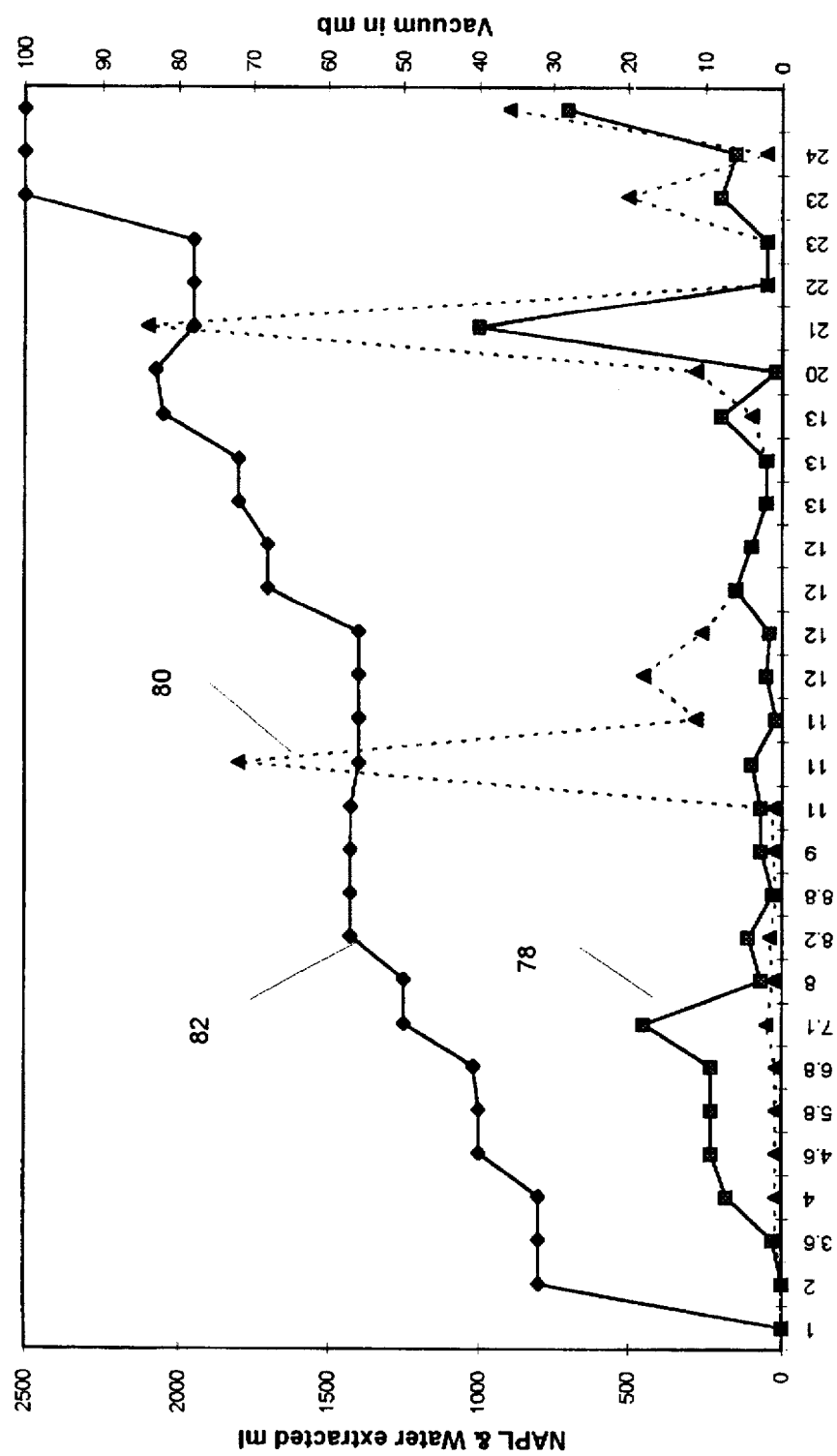
FIG. 5 is a plot on x-y coordinates of the volume of NAPL and water extracted in ml and the amount of vacuum in mb versus the time in hours of vacuum.

The rate of NAPL and water recovery at various vacuum rates versus time are depicted in the x-y plot of FIG. 5, wherein Curve 78 represents NAPL recovery in milliliters, Curve 80 represents water recovery in milliliters, and Curve 82 represents the vacuum rate in mb. A maximum free-product retrieval rate of 53% NAPL was achieved from a total spill volume of 9 liters, by progressively increasing vacuum rates in steps of 0, 37 mb, 57 mb, 78 mb, and 100 mb over a total duration of 30 hours. Lower vacuum rates of 57 mb and 78 mb resulted in NAPL recovery rates of 18% and 42% respectively. NAPL recovery in this pilot-scale experiment was performed by skimming free-product from the top of the simulated VER well 20. FIG. 4D illustrates the effectiveness of NAPL removal by VER after 28 hours of vacuum extraction. At 28 hours, the residual NAPL saturation over this area was generally reduced to 0.20. The rest of the cell 10 had NAPL saturations below the 0.10. About 0.10 in NAPL saturation was found in the water table.

While the above data and figures are helpful in the assessment of the feasibility of a VER program for NAPL remediation, the present method and apparatus are also useful in the calibration of three-phase models for the optimization of vacuum enhanced recovery of NAPL from remediation sites with complex hydrogeology and heterogeneous soils. In general, a sequential approach would be used, in which data of increasing complexity was used to make predictions using the computer model, whereupon the predictions are compared with the measured results from the present method and apparatus. Using that comparison, refinements may be made to the computer model to improve model parameters, until satisfactory agreement with the experimental data is obtained.

In sum, the above example illustrates the use of the pilot-scale laboratory soil cell 10 and an automated dual-energy gamma ray attenuation system 36 for the feasibility assessment of VER and optimization of three-phase remediation models to remediate free-product NAPL spills. As illustrated, the dynamic laboratory method determines the spatial distributions of three-phase fluid saturations of an oil spill simulation from the surface as it migrates through the vadose zone during the sequential stages of infiltration, redistribution and VER. A mean difference of 0.97% was achieved by comparing gamma-system measured NAPL retention volumes in the soil with that derived by the VER system, thereby demonstrating the accuracy of the disclosed method. The above example therefore illustrates the usefulness of the disclosed method and apparatus in assessing the feasibility of vacuum-enhanced recovery of NAPL from a heterogeneous soil in the vadose zone and the optimization of three-phase remediation models for NAPL recovery and remediation.

INDUSTRIAL APPLICABILITY

The present method and apparatus are expected to find use in the remediation of subsurface contamination by NAPLs as predictors of the reliability and accuracy of vacuum-induced clean-up methods and models. Additionally, the present method and apparatus may also find use in the petroleum industry for the study of oil and gas recovery from hydrocarbon reservoirs.

Thus, there has been disclosed a method and apparatus for determining the spatial distribution of fluids in a porous media contained in a three-dimensional cell as such fluids migrate through the porous media in response to a vacuum-induced pressure differential. Additionally, there has been disclosed a method of using the apparatus for the assessment of feasibility of vacuum-induced recovery of NAPLs from porous media. It will be readily apparent to those skilled in the art that various changes and modifications of an obvious nature may be made without departing from the spirit of the invention, and all such changes and modifications are considered to fall within the scope of the invention as defined by the appended claims.

What is claimed is:

1. A method for determining the spatial distribution of fluids in a porous media contained in a three-dimensional cell as said fluids migrate through said porous media in response to a vacuum-induced pressure differential, comprising the steps of, (a) providing a three-dimensional cell having a front side and a back side, each of which are at least semi-transparent and vertically disposed;

(b) installing at least two slotted casing wells at opposing ends of said cell, at least one first slotted casing well capable of being de-pressurized and at least one second slotted casing well capable of allowing air entry into said cell;

(c) filling said cell with a porous media;

(d) introducing at least one fluid into said filled cell and allowing said fluid to infiltrate said porous media;

(e) sealing said infiltrated, filled cell;

(f) de-pressurizing said at least one first slotted casing, thereby creating a negative pressure gradient across said infiltrated, filled cell;

(g) collimating a beam of gamma or X-ray radiation on said front side of said infiltrated, filled cell at each location of interest across the plane of said front side of said three-dimensional cell; and (h) measuring the amount of said radiation exiting said back side of said infiltrated, filled cell at each said location of interest and therefrom determining the saturation of said at least one fluid in said porous media at each location of interest across the plane of said front side of said three-dimensional cell.

2. The method of claim 1 wherein said front side and said back side of said three-dimensional cell comprise semi-transparent plastic that is resistant to attack by said at least one fluid.

3. The method of claim 1 wherein said three-dimensional cell further comprises a metal frame to prevent said front and back sides from bulging under pressure from said porous media.

4. The method of claim 1 wherein said porous media comprises naturally-occurring earth materials.

5. The method of claim 4 wherein said naturally-occurring earth material is at least one soil selected from the group consisting of clay, sand, and silt.

6. The method of claim 1 wherein said at least one fluid comprises air, water, and a non-aqueous phase liquid.

7. The method of claim 1 wherein said radiation in step (g) is provided using a system selected from the group consisting of a dual-energy gamma attenuation system and an X-ray fluorescence system.

8. The method of claim 7 wherein said dual-energy gamma attenuation system employs $^{137}$Cs and $^{241}$Am.

9. The method of claim 1 wherein said desired locations for measuring said fluid saturations comprise a matrix of points across said plane of said front side of said three-dimensional cell.

10. An apparatus for determining the spatial distribution of fluid in porous media in response to vacuum-induced pressure differential, including:

(a) a three-dimensional cell having a front side and a back side, each of which are at least semi-transparent and venially disposed said three-dimensional cell comprising a material which defines an opening for introduction of fluid thereinto, said three-dimensional cell capable of being sealed;

(b) at least two slotted casing wells at opposing ends of said cell, at least one first slotted casing well capable of being de-pressurized and at least one second slotted casing well capable of allowing air entry into said cell;

(c) at least one porous media contained within said three-dimensional cell;

(d) a means for collimating a beam of gamma or X-ray radiation on said front side of said cell at each location of interest across the plane of said front side of said cell; and (e) a means for measuring the amount of said radiation exiting said back side of said cell at each said location of interest, wherefrom the fluid saturations may be determined in said porous media of at least one fluid introduced into said three-dimensional cell by means of said opening in said three-dimensional cell.

11. The apparatus of claim 10 wherein said front side and said back side of said three-dimensional cell comprise semi-transparent plastic that is resistant to attack by said at least one fluid.

12. The apparatus of claim 10 wherein said apparatus further comprises a means for measuring the fluid recovery rate of said at least one fluid as recovered from said at least one first slotted casing well.

13. The apparatus of claim 10 wherein said three-dimensional cell further comprises a metal frame to prevent said front and back sides from bulging under pressure from said porous media.

14. The apparatus of claim 10 wherein said porous media comprises naturally-occurring earth materials.

15. The apparatus of claim 14 wherein said naturally-occurring earth material is at least one soil selected from the group consisting of clay, sand, and silt.

16. The apparatus of claim 10 wherein said beam of radiation is provided by a source selected from the group consisting of a dual-energy gamma attenuation system and an X-ray fluorescence system.

17. The apparatus of claim 16 wherein said dual-energy gamma attenuation system employs $^{137}$Cs and $^{241}$Am.

* * * * *